(12) United States Patent
Chen et al.

(10) Patent No.: US 10,159,701 B2
(45) Date of Patent: Dec. 25, 2018

(54) METHOD OF TREATING BONE LOSS

(71) Applicant: GENMONT BIOTECH INC., Tainan (TW)

(72) Inventors: Yi-Hsing Chen, Tainan (TW); Wan-Hua Tsai, Kaohsiung (TW); Chia-Hsuan Chou, Tainan (TW); Pei-Jane Tsai, Tainan (TW); Tsuei Yin Huang, Tainan (TW)

(73) Assignee: GENMONT BIOTECH INC., Tainan (TW)

( * ) Notice: Subject to any disclaimer, the term of this patent is extended or adjusted under 35 U.S.C. 154(b) by 0 days.

(21) Appl. No.: 15/825,155

(22) Filed: Nov. 29, 2017

(65) Prior Publication Data

US 2018/0256654 A1    Sep. 13, 2018

(30) Foreign Application Priority Data

Mar. 7, 2017 (TW) .............................. 106107470 A
Jul. 7, 2017 (TW) .............................. 106122946 A (51) Int. Cl.
*A23L 33/135* (2016.01)
*A61K 35/747* (2015.01)
*C12R 1/245* (2006.01)

(52) U.S. Cl.
CPC .......... *A61K 35/747* (2013.01); *A23L 33/135* (2016.08); *C12R 1/245* (2013.01); *A23V 2002/00* (2013.01); *A23V 2200/306* (2013.01)

(58) Field of Classification Search
None
See application file for complete search history.

(56) References Cited

U.S. PATENT DOCUMENTS

2016/0067289 A1    3/2016    Berggren et al.

FOREIGN PATENT DOCUMENTS

| CN | 105188723 A | 12/2015 |
| JP | 2009114111 | * 5/2009 |

OTHER PUBLICATIONS

Machine transation, JP2909114112, (2009).*
Ohlsson et al., PLOS ONE, 2014, vol. 9, Issue 3, pp. 1-8.*
Jau-Yi Li et al, (2016). Sex steroid deficiency-associated bone loss is microbiota dependent and prevented by probiotics. The journal of Clinical Investigation, vol. 126 No. 6, Jun. 2015.

* cited by examiner

*Primary Examiner* — Irene Marx
(74) *Attorney, Agent, or Firm* — Soroker Agmon Nordman (57) ABSTRACT

A use of a *Lactobacillus paracasei* strain to prepare a composition for resisting bone loss is provided. The *Lactobacillus paracasei* strain GMNL-653 is capable of promoting the expression of TGF-β and IL-10, while inhibiting the expression of osteoclast related genes and reducing the content of IL-17A in serum, so that the bone loss is slowed down.

3 Claims, 2 Drawing Sheets
Specification includes a Sequence Listing.

METHOD OF TREATING BONE LOSS

CROSS REFERENCE TO RELATED APPLICATIONS

This application claims the benefit of the filing date of Taiwan patent application No. 106107470, filed on Mar. 7, 2017, and Taiwan patent application No. 106122946, filed on Jul. 7, 2017, the disclosures of which are incorporated herein by reference.

FIELD OF THE INVENTION

The present disclosure relates to a use of a *Lactobacillus paracasei* strain to prepare a composition for resisting bone loss, and in particular relates to a use of a *Lactobacillus paracasei* strain GMNL-653 which has an ability of increasing the expression of osteogenic genes, inhibiting the expression of osteoclast related gene RANKL, and reducing the content of interleukin-17A in serum, to prepare a composition for resisting bone loss.

BACKGROUND OF THE INVENTION

Osteoporosis is a kind of systemic skeletal disease, which includes bone loss and bone microstructure deterioration, resulting in bone fragility and risk of fracture.

During a bone remodeling process, the bone formation of osteoblasts and bone resorption of osteoclasts maintain the dynamic balance of bone tissue together. Once the bone resorption is over bone formation, bone loss will be caused, and finally result in osteoporosis. In general, osteoporosis can be divided into postmenopausal osteoporosis and senile osteoporosis. Postmenopausal osteoporosis is common in women after menopause, due to the rapid reduction of estrogen in the female body, so that the osteoclast activity is increased to absorb the trabecular bone, and ultimately make the trabecular bone thin, break off, and make the number of bone cells reduce or be discontinuous, resulting in a reduction of bone strength. Senile osteoporosis is caused by the decline of osteogenic cell function, insufficient calcium and vitamin D intake, and intestinal absorption dysfunction, leading to, reduced bone synthesis, thick, loose cortical bones, and trabecular bone disappearing, so that bone strength is significantly reduced.

According to its mechanism, the current drugs for prevention and treatment of osteoporosis and fracture can be divided into anti-osteoclast or anti-bone loss drugs, bone formation or promoting osteoblast drugs, and mixed type drugs. Anti-osteoclast drugs include calcium, vitamin D, calcitonin, bisphosphonates, estrogen receptor modulators, sex hormones, osteoclast enzyme inhibitors, and RANKL monoclonal antibodies. The mixed type drug is currently strontium salt only. The drugs that control osteoporosis are accompanied by some side effects. It is found in clinical trials that the use of drugs in combination has no additional effect, but they will resist each other, or increase the incidence or strength of the side effects. Therefore, the current guidelines for various prevention and treatment of osteoporosis do not recommended the use of two anti-loss reagents, or the use one anti-loss reagent together with one promoting osteoblast reagent.

The osteoporotic drugs clinically used in the elderly and menopausal women, such as Fosamax, Tevanate, Covaxin (bisphosphonates drugs), will cause serious necrosis of jaw bone joint if users do not pay attention to oral hygiene, or the users are subject to tooth extraction, or dental implant surgery. Recent studies have also found that it may cause adverse reactions including atypical femoral fracture.

Although some literature states that certain specific probiotic strains, for example: *L. reuteri* ATCC PTA 6475; *L. paracasei* DSM13434; *L. plantarum* DSM 15312, DSM 15313 and *B. longum*, have the ability to reduce bone loss in ovariectomized rats, but they are applied in the form of live bacteria in the experiments, and it is found that the ability to slow down bone loss is achieved by reducing inflammation. The live bacteria are affected by stomach acid, bile salt, and antibiotics, and thus the use of the abovementioned probiotic strains is more limited. In addition, the number of viable bacteria is susceptible to preservation conditions, such as temperature, humidity, so that the product dosage form is also more restricted.

It is therefore necessary to provide a use of a strain to prepare a composition for resisting bone loss, in order to solve the problems existing in the conventional technology as described above.

SUMMARY OF THE INVENTION

A primary object of the present disclosure is to provide a use of *Lactobacillus paracasei* strain GMNL-653 to prepare a composition for resisting bone loss. The *Lactobacillus paracasei* strain GMNL-653 and the composition can be administrated through any possible pathway in order to enter the digestive system to increase the gene expression of osteogenesis-related cytokine TGF-β and IL-10, inhibit the expression of osteoclast related genes (such as RANKL), and reduce the content of the bone loss related cytokine IL-17A in serum, thereby solving the problem caused by bone loss.

To achieve the above objects, the present disclosure provides a use of *Lactobacillus paracasei* strain to prepare a composition for resisting bone loss, comprising a *Lactobacillus paracasei* strain GMNL-653 deposited in the China Center for Type Culture Collection (CCTCC) with an accession number of CCTCC M2016226.

In one embodiment of the present disclosure, *Lactobacillus paracasei* strain GMNL-653 is a dead strain.

In one embodiment of the present disclosure, the *Lactobacillus paracasei* strain GMNL-653 is a thermal death strain.

In one embodiment of the present disclosure, the *Lactobacillus paracasei* strain GMNL-653 has an ability of reducing the content of interleukin-17A (IL-17) in serum.

In one embodiment of the present disclosure, the *Lactobacillus paracasei* strain GMNL-653 has an ability of increasing the expression of interleukin-10 (IL-10).

In one embodiment of the present disclosure, the *Lactobacillus paracasei* strain GMNL-653 has an ability of increasing the expression of TGF-β.

In one embodiment of the present disclosure, the *Lactobacillus paracasei* strain GMNL-653 has an ability of inhibiting the expression of osteoclast related gene RANKL.

In one embodiment of the present disclosure, the composition is a pharmaceutical composition, a nutritional supplement, a health food, a medical food, or the combination thereof.

In one embodiment of the present disclosure, the composition further comprises a carrier to form the composition into tablets, capsules, powders, or oral liquid preparations.

DETAILED DESCRIPTION OF THE PREFERRED EMBODIMENTS

The structure and the technical means adopted by the present disclosure to achieve the above and other objects can be best understood by referring to the following detailed description of the preferred embodiments. Furthermore, if there is no specific description in the disclosure, singular terms such as "a", "one", and "the" include the plural number. For example, "a compound" or "at least one compound" may include a plurality of compounds, and the mixtures thereof. If there is no specific description in the disclosure, "%" means "weight percentage (wt %)", and the numerical range (e.g., 10%-11% of A) contains the upper and lower limit (i.e., 10%≤A≤11%). If the lower limit is not defined in the range (e.g., less than, or below 0.2% of B), it means that the lower limit may be 0 (i.e., 0%≤B≤0.2%). The proportion of "weight percent" of each component can be replaced by the proportion of "weight portion" thereof. The abovementioned terms are used to describe and understand the present disclosure, but the present disclosure is not limited thereto.

One embodiment of the present disclosure provides a *Lactobacillus paracasei* strain for resisting bone loss and a use of the strain to produce a composition for resisting bone loss. The *Lactobacillus paracasei* strain is referred to as *Lactobacillus paracasei* strain GMNL-653, which is deposited in the China Center for Type Culture Collection (CCTCC) with an accession number of CCTCC M2016226. The *Lactobacillus paracasei* strain GMNL-653 can be a viable strain or a dead strain, for example a thermal dead strain. The *Lactobacillus paracasei* strain GMNL-653 has an anti-inflammatory ability, and can inhibit the expression of osteoclast related gene RANKL and formation of interleukin-17A (IL-17A).

One embodiment of the present disclosure provides a composition for resisting bone loss, comprising the abovementioned *Lactobacillus paracasei* strain GMNL-653. Preferably, the composition can be a pharmaceutical composition, a nutritional supplement, a health food, a medical food, or the combination thereof. The composition can be formed in various form based on the effectivity or convenience, for example, a carrier is used for forming the composition into tablets, capsules, powders, or oral liquid preparations, but it is not limited thereto. The composition can be formed into any pharmacologically or physiologically acceptable form. In addition, the composition is preferably administered by means of food to enter the digestive system, so that the *Lactobacillus paracasei* strain GMNL-653 can exert its effect in the digestive system.

The *Lactobacillus paracasei* strain GMNL-653 in the abovementioned embodiments is one of a plurality of isolates mainly isolated from human intestines. The primers (SEQ ID NO: 1 and SEQ ID NO: 2) listed in Table 1 are used to perform PCR to reproduce 16S rDNA segments of each isolate, and then sequencing the 16S rDNA segment of each isolate. After sequencing, a 16S rDNA gene sequence of one of the isolates can be obtained as below (SEQ ID NO: 3); subsequently, from the comparison results on the NCBI website, it shows that the 16S rDNA sequences of the isolates are similar to that of the *Lactobacillus paracasei* strains with identities all over 99%, so that the strain GMNL-653 indeed belongs to the *Lactobacillus paracasei* genus.

TABLE 1

| PCR primer | | |
|---|---|---|
| Primer | SEQ ID NO: | SEQ |
| PAF | 1 | AGA GTT TGA TCC TGG CTC AG |
| 536R | 2 | GTA TTA CCG CGG CTG CTG |

A complete 16S rDNA sequence (SEQ ID NO: 3 of the *Lactobacillus paracasei* strain GMNL-653 is listed as below:

CGGAGGCCCCTATGATGGGCGTCGTACGAGTTCTCGTTGATGATCGGTGC

TTGCACCGAGATTCTCATGGAACGAGTGGCGGACGGGTGAGTAACACGTG

GGTAACCTGCCCTTAAGTGGGGGATAACATTTGGAAACAGATGCTAATAC

CGCATAGATCCTGTAACCGCATGGTTCTTGGCTGATAGATGGCGTAAGCT

ATCGCTGTTGGATGGACCCGCGGCGTATTATCTAGTTGGTGAGGTAGTGG

CTCACCGAGGCCATGATACGTATCCGAGCTGAGAGGTTGATGGGCGAGTT

TGTGACTGAGACACGTCCCAAACTACTACGGGAGGCAGCAGTAGGGAATC

TTCCACAATGGACGCAAGTCTGATGGAGCAACGCCGCGTGAGTGAAGAAG

GCTTTCGGGTCGTAAAACTCTGTTGTTGGAGAAGAATGGTCGGCAGAGTA

ACTGTTGTCGGCGTGACGGTATCCAACCAGAAAGCCACGGCTAACTACGT

GCCAGCAGCCGGGGGTAATACA

A fermentation test of the *Lactobacillus Paracasei* strain GMNL-653 is carried out to obtain the results shown in Table 2.

TABLE 2

| Fermentation Test | | |
|---|---|---|
| Strips No. | carbohydrates substrate | GMNL-653 |
| 0 | CONTROL | − |
| 1 | Glycerol | − |
| 2 | Erythritol | − |
| 3 | D-Arabinose | − |
| 4 | L-Arabinose | − |
| 5 | D-Ribose | + |
| 6 | D-Xylose | − |
| 7 | L-Xylose | − |
| 8 | D-Adonitol | − |
| 9 | Methyl-β-D-Xylopyranoside | − |
| 10 | D-Galactose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | − |
| 20 | Methyl-α-D-mannopyranoside | − |
| 21 | Methyl-α-D-glucopyranoside | + |

TABLE 2-continued

Fermentation Test

| Strips No. | carbohydrates substrate | GMNL-653 |
|---|---|---|
| 22 | N-Acetyl glucosamine | + |
| 23 | Amygdalin | − |
| 24 | Arbutin | + |
| 25 | Esculin ferric citrate | + |
| 26 | Salicin | + |
| 27 | D-Cellobiose | + |
| 28 | D-Maltose | + |
| 29 | D-Lactose (bovine origin) | − |
| 30 | D-Melibiose | − |
| 31 | D-Saccharose (sucrose) | + |
| 32 | D-Trehalose | + |
| 33 | Inulin | − |
| 34 | D-Melezitose | + |
| 35 | D-Raffinose | − |
| 36 | Amidon (starch) | − |
| 37 | Glycogen | − |
| 38 | Xylitol | − |
| 39 | Gentiobiose | − |
| 40 | D-Turanose | + |
| 41 | D-Lyxose | − |
| 42 | D-Tagatose | + |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-ketogluconate | − |
| 49 | Potassium 5-ketogluconate | − |

−: negative;
+: positive

To verify the anti-inflammatory ability of the *Lactobacillus paracasei* strain GMNL-653 according to the present disclosure, and to confirm that the *Lactobacillus Paracasei* strain GMNL-653 can inhibit the bone loss, experiments 1 to 3 are executed.

Experiment 1: Bone Tissue Analysis

Strain: *Lactobacillus paracasei* Strain GMNL-653

Strain Treatment:

Preparation of dead bacteria: 1 μl *Lactobacillus paracasei* strain GMNL-653 and the *Lactobacillus salivarius* strain GMNL-678 frozen viral was inoculated to 1 ml of MRS broth, respectively, and aerobically incubated at 37° C. for 20 hours (first activation). The next day, adding 15 μl culture solution (first activation) into 1.5 ml of MRS broth, and then and aerobically incubated at 37° C. for 20 hours (secondary activation) Estimating the bacteria number by using OD 600 nm to adjust the bacteria concentration to $4.1 \times 10^8$ CFU/ml, and heat-killed bacteria was carried by autoclaving at 121° C. for 15 minutes.

Osteoporosis Mouse Model:

8-week-old ICR female mice were purchased from Bio-LASCO Taiwan Co., Ltd. and ovariectomy was performed when they were 9 week-old. The mice underwent anesthesia and were ovariectomized through back on both sides of the ovaries. All groups were given the test substance by oral gavage at 4 days after surgery. The groups were divided into a sham operation group (control group, their abdominal cavities were cut but their ovaries were not removed); and 4 ovariectomized groups (Ovariectomy; OVX). When the mice were sacrificed, the ovarian tissues were checked and confirmed whether the removal of ovarian was successful. The experimental results of the mice under failed operation were not used. In the 4 groups of the ovariectomized mice, one group was the vehicle group ($H_2O$ group), and one group was the positive drug group (anti-osteoporosis drug, Alendronate). Alendronate was formulated with deionized water at a concentration of 0.25 mg/ml. The mice were given 0.1 ml drug per 10 grams of body weight and 4 times a week. The remaining two groups were fed with 0.2 ml of dead GMNL-653, and dead GMNL-678, respectively (strain concentration is $4.1 \times 10^8$ cells/ml; daily dose of the mouse is $8.2 \times 10^7$ cells/mouse, the human dose is $2 \times 10^{10}$ cells/60 kg adult). The two groups were oral gavage probioyic once/day until 28 days. The mice were anesthetized and sacrificed for intraperitoneal cephalic vein sampling, and each femur was removed for analysis.

Analysis Method:

Micro computed tomography (SkyScan 1076, Kontizh, Belgium, with resolution of 18 μm) was taken of the backbone of the right femur far from the end was taken, and the trabecular bone volume ratio (i.e. bone volume/tissue volume; BV/TV) was analyzed by a software. The analyzed position was selected to include the area of 100 pieces under the growth plate excluding cortical bone. The bone mineral density analysis was applied to the same area. The obtained data in the experiments were analyzed with two-way analysis of variance, and the T-test statistical analysis. All data were presented as mean±SD. After comparisons, the above-mentioned groups were analyzed statistically and noted by different marks to represent the statistically significant differences (* represents p<0.05; ** represents p<0.01 See Table 3 and Table 4, showing the results of the experiment 1.

TABLE 3

Trabecular bone volume ratio (BV/TV, bone volume/tissue volume) BV/TV (%)

| Control | OVX + $H_2O$ | OVX + GMNL-653 Dead | OVX + GMNL-678 Dead | OVX + Alendronate |
|---|---|---|---|---|
| 42.12 ± 2.4** | 30.9 ± 1.1 | 36.80 ± 1.6** | 32.38 ± 0.8** | 34.88 ± 0.9** |

From table 3, after removing the ovaries, the trabecular bone volume ratio in (OVX+$H_2O$) group (disease group) was lower than the control group, which means that the osteoporosis animal model was successful. Comparing the dead GMNL-653 group, the dead GMNL-678 group, and the positive drug group with the control group, it can be found that BV/TV of the three group were higher than the disease group, which means that the GMNL-653, GMNL-678, and the drug Alendronate all indeed slow down bone loss to a certain degree after removing the ovaries. The group of the tube fed GMNL-653 strain even has slightly better protective effects than the anti-osteoporosis drug Alendronate.

TABLE 4

Femur bone mineral density (BMD, excluding cortical bone) BMD (g/cm³)

| Control | OVX + $H_2O$ | OVX + GMNL-653 Dead | OVX + GMNL-678 Dead | OVX + Alendronate |
|---|---|---|---|---|
| 0.502 ± 0.04** | 0.344 ± 0.04 | 0.444 ± 0.043** | 0.38 ± 0.027 * | 0.426 ± 0.02* |

From table 4, it can be noted that the disease group (OVX+$H_2O$) has lower BMD than the control group; in the groups of dead GMNL-653, the BMD is significantly higher than the BMD in the disease group (OVX+$H_2O$). That is, the group of the tube fed GMNL-653 strain can slow down bone loss of the mice after removing the ovarian, and the protection effect of the GMNL-653 is better than the GMNL-678.

Experiment 2: Effects of GMNL-653 on Osteoclast Genes, and Cytokines

Extraction of tibial RNA: The left femurs of the mice were removed, cut into small pieces with scissors, and an appropriate amount of liquid nitrogen was added to grind the bones quickly. 0.5 ml TRizol® Reagent was added to the ground bone powder to extract RNA; 0.1 ml chloroform was then added thereto to turn up and down 15 times. The solution was placed at room temperature to react for 5 minutes, followed by centrifugalized and extracted the upper layer to new eppendorf; 0.25 ml isopropanol was added thereto and the solution was placed at room temperature for 10 minutes and then centrifugalized; the supernatant was removed and the precipitate was washed with 0.5 ml 75% ethanol; after the precipitate was dried, 20-50 µl DEPC water was added to dissolve the precipitate and the RNA concentration was measured.

RNA reverse transcription cDNA: 1-5 µg RNA was obtained and RNase-free water was added therein to 10 µl; additionally, 10× Random primer (2 µl), 10 mM dNTP (1 µl) were added, at 65° C. for 5 minutes, and on ice for 2-3 minutes; after first stage interaction, additional 5×RT buffer (4 µl), 0.1M DTT (1 µl), RNase inhibitor (Invitrogen, RNaseOUT™, 1 µl), RT enzyme (Invitrogen, SuperScript®III, 1 µl) were added and mixed at room temperature for 5 minutes, and then placed at 50° C. for 60 minutes, at 70° C. for 15 minutes, to proceed the enzyme reverse transcription.

Tibial cDNA in real-time PCR analysis: 1 µl tibial cDNA was obtained and added 4 µl of 1 µM F+R primers (forward/reverse primers are listed below), and 5 µl of 2× Rotor-Gene SYBR Green PCR Master Mix (Qiagen, Cat. 204076), placed into Q-PCR apparatus to react. The relative expression of TGF-β and RANKL were obtained by deducting the GAPDH itself.

TABLE 5

| Primers | | |
|---|---|---|
| TGF-β Forward primer | SEQ ID NO: 4 | GAGTAACGCTTTCCGGAGTC |
| TGF-β Reverse primer | SEQ ID NO: 5 | ACAGTCACCAGCATCTCAGC |
| RANKL Forward primer | SEQ ID NO: 6 | CGTACCTGCGGACTATCTTCA |
| RANKL Reverse primer | SEQ ID NO: 7 | CTTGGACACCTGGACGCTAA |
| IL-10 Forward primer | SEQ ID NO: 8 | GGTTGCCAAGCCTTATCGGA |
| IL-10 Reverse primer | SEQ ID NO: 9 | ACCTGCTCCACTGCCTTGCT |
| GAPDH Forward primer | SEQ ID NO: 10 | GCACAGTCAAGGCCGAGAAT |
| GAPDH Reverse primer | SEQ ID NO: 11 | GCCTTCTCCATGGTGGTGAA |

Analysis method: The obtained data in the experiments were analyzed with two-way analysis of variance, and executed T-test statistical analysis. The abovementioned groups were analyzed statistically compared with the OVX+H$_2$O group, wherein * represents $p<0.05$; ** represents $p<0.01$.

Figure 1:
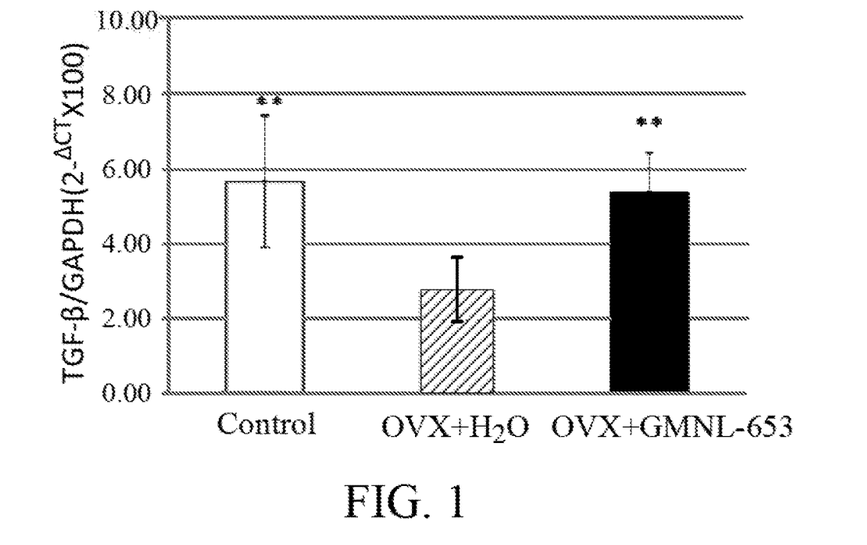
FIG. 1 is a diagram showing the expression of TGF-β of each group in the experiment 2 according to one embodiment of the present disclosure.

As shown in FIG. 1, GMNL-653 dead strain can increase the expression of TGF-β which can protect bone against bone loss. Comparing the mice of the control group with the disease group (OVX+H$_2$O), the expression of osteoblast-related cytokine TGF-β of the disease group is significantly reduced; the mice fed with GMNL-653 have significant increased expression of TGF-β compared with the disease group (OVX+H$_2$O). This result means that the GMNL-653 strain has ability of promoting the expression of TGF so as to slow down bone loss.

Figure 2:
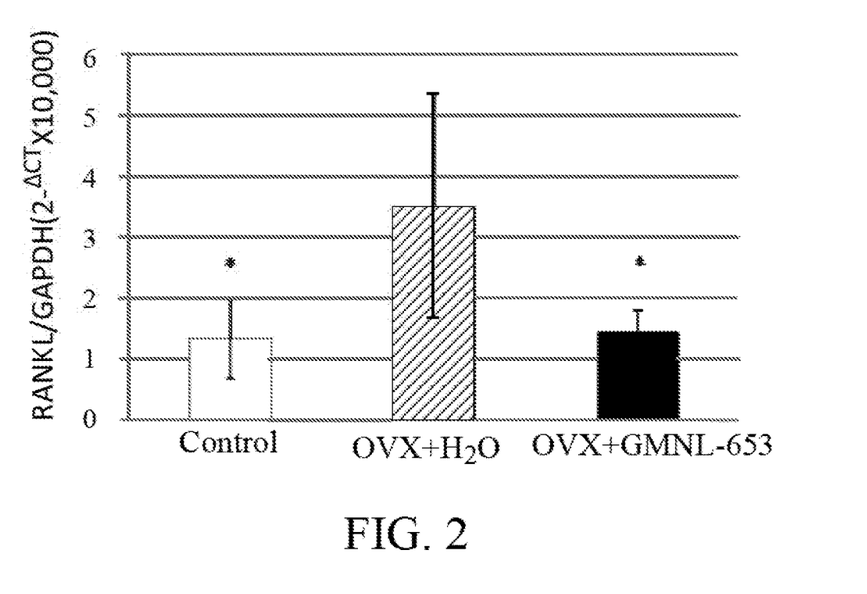
FIG. 2 is a diagram showing the expression of osteoclast related gene RANKL of each group in the experiment 2 according to one embodiment of the present disclosure.

Next, as shown in FIG. 2, the expression of osteoclasts-related gene RANKL in the disease group (OVX+H$_2$O) are higher than the control group, while in the groups of the mice given the dead strain GMNL-653 after removing ovarian, the expression of RANKL is lower than the the disease group. The result means that the GMNL-653 has an ability to inhibit the expression of RANKL, thereby slowing down bone loss.

Figure 3:
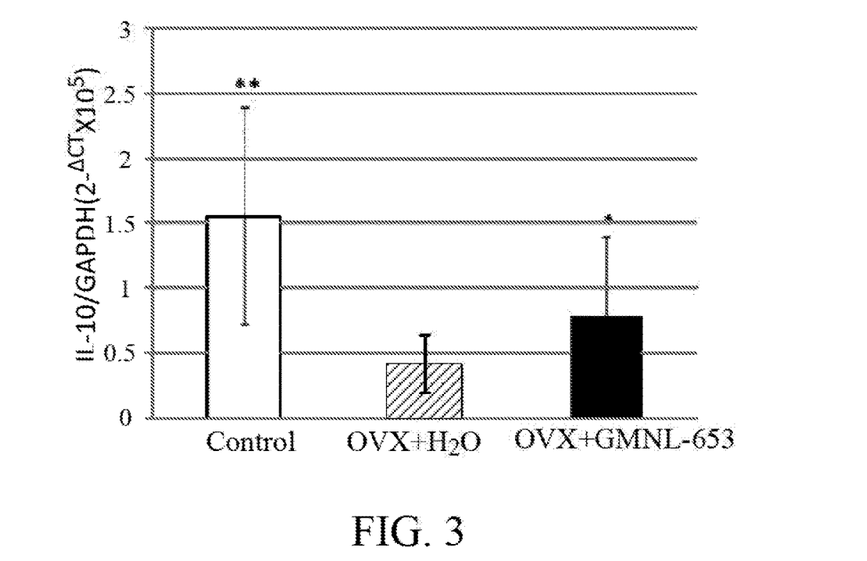
FIG. 3 is a diagram showing the expression of interleukin-10 (IL-10) of each group in the experiment 2 according to one embodiment of the present disclosure.

Refer to FIG. 3, it can be observed that the dead strain GMNL-653 increases the expression of the cytokine IL-10. Compared with the mice in the sham operation group (Control group), the expression of the anti-inflammatory cytokine IL-10 in the disease group (OVX+H$_2$O) is significantly reduced; while in the groups of dead strain GMNL-653, the expression of IL-10 is significantly increased compared with the disease group (OVX+H$_2$O). That is, the GMNL-653 strain has an ability to promote the expression of IL-10 so as to slow down bone loss.

Experiment 3: Effects of GMNL-653 on Osteoclasts Related Cytokine IL-17A

Analysis method: the mice of each group were sacrificed with anesthesia. The blood of the sacrificed mice was gathered and stood at room temperature for 30 minutes. Subsequently, the gathered blood was centrifuged at 10,000 g for 10 minutes to gather the serum, and the serum was individually packed and stored at −80'C. The analysis of IL-17A was performed by an antigen-antibody binding reaction on the original serum, and run the analysis experiment with BioLegend's ELISA MAX™ Deluxe Sets. The experiment steps were followed by the original instructions. Finally, the absorbance of OD 450 nm was measured by ELISA reader. The measurement of each group was repeated twice.

Figure 4:
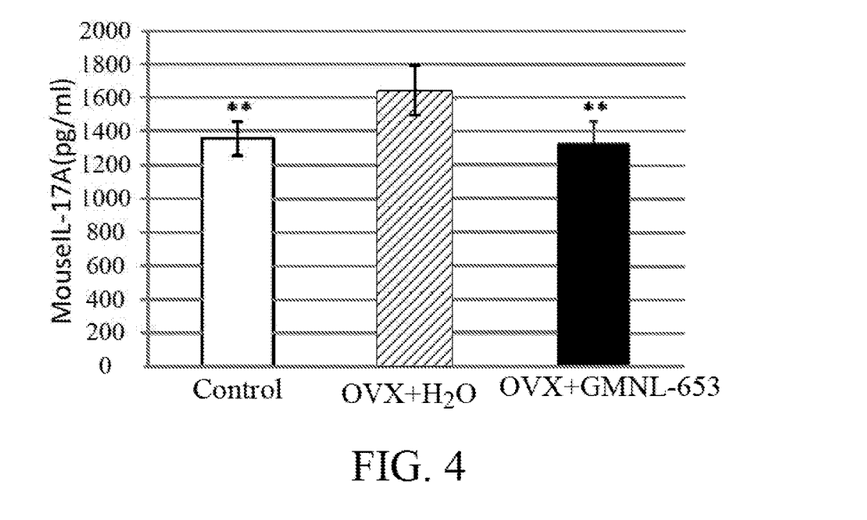
FIG. 4 is a diagram showing the interleukin-17A (IL-17A) content in serum of each group in the experiment 3 according to one embodiment of the present disclosure.

The analysis result is shown in FIG. 4. After removing ovaries, the content of the IL-17A in serum of the mice in the disease group (OVX+H$_2$O) is increased as compared with the sham group (control), but the content of IL-17A in serum is apparently reduced in the GMNL-653 dead strain group. The abovementioned groups were analyzed statistically compared with, the OVX+H$_2$O group, wherein * represents $p<0.05$; ** represents $p<0.01$.

In summary, according to the above results, it is certain that the *Lactobacillus paracasei* strain GMNL-653 in the dead form can significantly slow down bone loss of the mice after removing ovaries in the bone tissue analysis (trabecular bone volume ratio, BV/TV) and bone mineral density (BMD) of animal experiments. It is reported that the TGF-β plays an important role during the procedure of intracartilanginous ossification or endochondral ossification, and the mice with defective TGF-β may reduce bone growth and bone mineralization. The IL-10 is an important cytokine related to anti-inflammation. It has been suggested that IL-10 may provide an indirect balance between the ionic ratio of $Ca^{2+}$ (calcium)/Pi (phosphorous); In addition, bone-loss related cytokine IL-17A has been shown to be associated with RANKL to be osteoclast precursor cells or induce the expression of osteoclasts in the mice lack of estrogen so as to carry out the multi-core reaction, so that the proliferation and differentiation of the osteoclasts are promoted. In rodents, the estrogen can inhibit the differentiation of the cells regulated by IL-17A, and further can inhibit the formation and mineralization of the osteoblasts. Therefore, the composition containing *Lactobacillus paracasei* strain GMNL-653 in the present disclosure can resist bone loss through increasing the expression of the osteoblast-related cytokine TGF-β and anti-inflammatory cytokine IL-10, inhibiting the expression of osteoclasts-related genes (e.g. RANKL), and reducing the quantity of cytokine IL-17A contained in serum to resist bone loss.

In addition, it can be found in the experiment results that the GMNL-653 has a better protective effect than the anti-osteoporosis drug "Alendronate". Alendronate has been found to have many side effects, including heart disease, stubborn pain, jaw osteonecrosis, fractures, and esophageal cancer. Therefore, the *Lactobacillus Paracasei* strain GMNL-653, safe and with no side effects, is applicable to slow down bone loss. It should be a better choice for the menopausal women in considering the future prevention and inhibition of bone loss.

The present disclosure has been described with preferred embodiments thereof and it is understood that many changes and modifications to the described embodiments can be carried out without departing from the scope and the spirit of the disclosure that is intended to be limited only by the appended claims.

SEQUENCE LISTING

```
<110> GENMONT BIOTECH INC.

<120> USE OF LACTOBACILLUS PARACASEI STRAIN GMNL-653 TO PREPARE COMPOSITION
      FOR RESISTING BONE LOSS

<130> TP170229-US

<160> 11

<170> PatentIn version 3.5

<210> 1
<211> 20
<212> DNA
<213> Artificial Sequence

<220>
<223> PAF primer

<400> 1
agagtttgat cctggctcag                                                    20

<210> 2
<211> 18
<212> DNA
<213> Artificial Sequence

<220>
<223> 536R primer

<400> 2
gtattaccgc ggctgctg                                                      18

<210> 3
<211> 523
<212> DNA
<213> Artificial Sequence

<220>
<223> Sequencing primer

<400> 3
cggaggcccc tatgatgggc gtcgtacgag ttctcgttga tgatcggtgc ttgcaccgag        60
attctcatgg aacgagtggc ggacgggtga gtaacacgtg ggtaacctgc ccttaagtgg       120
gggataacat ttggaaacag atgctaatac cgcatagatc ctgtaaccgc atggttcttg       180
gctgatagat ggcgtaagct atcgctgttg gatggacccg cggcgtatta tctagttggt       240
gaggtagtgg ctcaccgagg ccatgatacg tatccgagct gagaggttga tgggcgagtt       300
tgtgactgag acacgtccca aactactacg ggaggcagca gtagggaatc ttccacaatg       360
gacgcaagtc tgatggagca acgccgcgtg agtgaagaag gctttcgggt cgtaaaactc       420
tgttgttgga gaagaatggt cggcagagta actgttgtcg gcgtgacggt atccaaccag       480
aaagccacgg ctaactacgt gccagcagcc ggggggtaat aca                         523

<210> 4
<211> 20
<212> DNA
<213> Artificial Sequence

<220>
<223> TGF beta forward primer
```

SEQUENCE LISTING

-continued

<400> 4
gagtaacgct ttccggagtc          20

<210> 5
<211> 20
<212> DNA
<213> Artificial Sequence

<220>
<223> TGF beta reverse primer

<400> 5
acagtcacca gcatctcagc          20

<210> 6
<211> 21
<212> DNA
<213> Artificial Sequence

<220>
<223> RANKL forward primer

<400> 6
cgtacctgcg gactatcttc a        21

<210> 7
<211> 20
<212> DNA
<213> Artificial Sequence

<220>
<223> RANKL reverse primer

<400> 7
cttggacacc tggacgctaa          20

<210> 8
<211> 20
<212> DNA
<213> Artificial Sequence

<220>
<223> IL-10 forward primer

<400> 8
ggttgccaag ccttatcgga          20

<210> 9
<211> 20
<212> DNA
<213> Artificial Sequence

<220>
<223> IL-10 reverse primer

<400> 9
acctgctcca ctgccttgct          20

<210> 10
<211> 20
<212> DNA
<213> Artificial Sequence

<290>
<223> GAPDH forward primer

<400> 10
gcacagtcaa ggccgagaat          20

<210> 11
<211> 20
<212> DNA
<213> Artificial Sequence

SEQUENCE LISTING

<220>
<223> GAPDH reverse primer

<400> 11
gccttctcca tggtggtgaa                                                    20

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: PAF primer

<400> SEQUENCE: 1
agagtttgat cctggctcag                                                    20

<210> SEQ ID NO 2
<211> LENGTH: 18
<212> TYPE: DNA
<213> ORGANISM: Artificial Sequence
<220> FEATURE:
<223> OTHER INFORMATION: 536R primer

<400> SEQUENCE: 2
gtattaccgc ggctgctg                                                      18

<210> SEQ ID NO 3
<211> LENGTH: 523
<212> TYPE: DNA
<213> ORGANISM: Artificial Sequence
<220> FEATURE:
<223> OTHER INFORMATION: Sequencing primer

<400> SEQUENCE: 3
cggaggcccc tatgatgggc gtcgtacgag ttctcgttga tgatcggtgc ttgcaccgag        60
attctcatgg aacgagtggc ggacgggtga gtaacacgtg ggtaacctgc ccttaagtgg       120
gggataacat ttggaaacag atgctaatac cgcatagatc ctgtaaccgc atggttcttg       180
gctgatagat ggcgtaagct atcgctgttg gatggacccg cggcgtatta tctagttggt      240
gaggtagtgg ctcaccgagg ccatgatacg tatccgagct gagaggttga tgggcgagtt      300
tgtgactgag acacgtccca aactactacg ggaggcagca gtagggaatc ttccacaatg      360
gacgcaagtc tgatggagca acgccgcgtg agtgaagaag ctttcgggt cgtaaaactc       420 tgttgttgga gaagaatggt cggcagagta actgttgtcg gcgtgacggt atccaaccag      480
aaagccacgg ctaactacgt gccagcagcc gggggtaat aca                         523

<210> SEQ ID NO 4
<211> LENGTH: 20
<212> TYPE: DNA
<213> ORGANISM: Artificial Sequence
<220> FEATURE:
<223> OTHER INFORMATION: TGF beta forward primer

<400> SEQUENCE: 4
gagtaacgct ttccggagtc                                                    20

<210> SEQ ID NO 5
<211> LENGTH: 20
<212> TYPE: DNA
<213> ORGANISM: Artificial Sequence
<220> FEATURE:
<223> OTHER INFORMATION: TGF beta reverse primer

<400> SEQUENCE: 5
acagtcacca gcatctcagc                                                  20

<210> SEQ ID NO 6
<211> LENGTH: 21
<212> TYPE: DNA
<213> ORGANISM: Artificial Sequence
<220> FEATURE:
<223> OTHER INFORMATION: RANKL forward primer

<400> SEQUENCE: 6
cgtacctgcg gactatcttc a                                                21

<210> SEQ ID NO 7
<211> LENGTH: 20
<212> TYPE: DNA
<213> ORGANISM: Artificial Sequence
<220> FEATURE:
<223> OTHER INFORMATION: RANKL reverse primer

<400> SEQUENCE: 7
cttggacacc tggacgctaa                                                  20

<210> SEQ ID NO 8
<211> LENGTH: 20
<212> TYPE: DNA
<213> ORGANISM: Artificial Sequence
<220> FEATURE:
<223> OTHER INFORMATION: IL-10 forward primer

<400> SEQUENCE: 8
ggttgccaag ccttatcgga                                                  20

<210> SEQ ID NO 9
<211> LENGTH: 20
<212> TYPE: DNA
<213> ORGANISM: Artificial Sequence
<220> FEATURE:
<223> OTHER INFORMATION: IL-10 reverse primer

<400> SEQUENCE: 9
acctgctcca ctgccttgct                                                  20

<210> SEQ ID NO 10
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 10
gcacagtcaa ggccgagaat                                                  20

<210> SEQ ID NO 11
<211> LENGTH: 20
<212> TYPE: DNA
<213> ORGANISM: Artificial Sequence
<220> FEATURE:

-continued

```
<223> OTHER INFORMATION: GAPDH reverse primer

<400> SEQUENCE: 11
gccttctcca tggtggtgaa                                                20
```

What is claimed is:

1. A method of treating bone loss, comprising:
administering to subject in need thereof, an effective amount of a composition comprising *Lactobacillus paracasei* GMNL-653 and a pharmaceutically acceptable carrier, wherein the *Lactobacillus paracasei* GMNL-653 is deposited in the China Center for Type Culture Collection (CCTCC) with an accession number of CCTCC M2016226 on 25 Apr. 2016, wherein the *Lactobacillus paracasei* GMNL-653 is dead, reduces the content of interleukin-17A in serum inhibits the expression of osteoclast-related gene RANKL.

2. The method according to claim 1, wherein the *Lactobacillus paracasei* GMNL-653 increases the expression of TGF-$\beta$.

3. The method according to claim 1, wherein the composition is a pharmaceutical composition, a nutritional supplement, a health food, a medical food, or a combination thereof.

* * * * *